United States Patent
Kazuno et al.

(10) Patent No.: US 9,527,833 B2
(45) Date of Patent: Dec. 27, 2016

(54) STABLE CRYSTAL FORM OF TIPIRACIL HYDROCHLORIDE AND CRYSTALLIZATION METHOD FOR THE SAME

(71) Applicant: TAIHO PHARMACEUTICAL CO., LTD., Tokyo (JP)

(72) Inventors: Hideki Kazuno, Ibaraki (JP); Tomonobu Mutsumi, Saitama (JP)

(73) Assignee: TAIHO PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/896,748

(22) PCT Filed: Jun. 17, 2014

(86) PCT No.: PCT/JP2014/065985
§ 371 (c)(1),
(2) Date: Dec. 8, 2015

(87) PCT Pub. No.: WO2014/203877
PCT Pub. Date: Dec. 24, 2014

(65) Prior Publication Data
US 2016/0145241 A1    May 26, 2016

(30) Foreign Application Priority Data
Jun. 17, 2013  (JP) ................. 2013-126567

(51) Int. Cl.
*C07D 403/06*  (2006.01)

(52) U.S. Cl.
CPC .................. *C07D 403/06* (2013.01)

(58) Field of Classification Search
None
See application file for complete search history.

(56) References Cited

U.S. PATENT DOCUMENTS

| 5,744,475 A | 4/1998 | Yano et al. |
| 6,159,969 A | 12/2000 | Yano et al. |
| 6,294,535 B1 * | 9/2001 | Yano .................. C07D 231/12 514/235.8 |
| 6,479,500 B1 | 11/2002 | Fukushima et al. |

FOREIGN PATENT DOCUMENTS

| CN | 1297350 | 5/2001 | |
| CN | 103788075 | 5/2014 | |
| JP | WO96/30346 | * 10/1996 | ........... C07D 239/54 |
| WO | 96/30346 | 10/1996 | |

OTHER PUBLICATIONS

Morissette et al. in Drug Delivery Reviews, 56 (2004) 275-300.*
International Preliminary Report on Patentability and Written Opinion of the International Searching Authority issued Dec. 22, 2015 in International (PCT) Application No. PCT/JP2014/065985.
Noriaki Hirayama, Yuki Kagobutsu Kessho Sakusei Handbook, 2008, pp. 10-11, 57-72 and 78-81, with partial English translation.
International Search Report issued Aug. 12, 2014 in International (PCT) Application No. PCT/JP2014/065985.
Yano et al., "Synthesis and evaluation of 6-methylene-bridged uracil derivatives. Part 2: Optimization of inhibitors of human thymidine phosphorylase and their selectivity with uridine phosphorylase", Bioorganic & Medicinal Chemistry, vol. 12, Issue 13, 2004, pp. 3443-3450.
Noriaki Hirayama, Yuki Kagobutsu Kessho Sakusei Handbook, 2008, pp. 10-11, 57-72 and 78-81.
Emura et al., "A novel combination antimetabolite, TAS-102, exhibits antitumor activity in FU-resistant human cancer cells through a mechanism involving FTD incorporation in DNA", International Journal of Oncology, vol. 25, 2004, pp. 571-578.
Overman et al., "Phase 1 study of TAS-102 administered once daily on a 5-day-per-week schedule in patients with solid tumors", Invest New Drugs, vol. 26 (5), 2008, pp. 445-454.
Full English Translation of CN103788075, May 2014.

* cited by examiner

*Primary Examiner* — Dennis Heyer
(74) *Attorney, Agent, or Firm* — Wenderoth, Lind & Ponack, L.L.P.

(57) ABSTRACT

An objective of the present invention is to obtain a stable crystal form of 5-chloro-6-(2-iminopyrrolidin-1-yl)methyl-2,4(1H,3H)-pyrimidinedione hydrochloride. The present invention provides a crystal of 5-chloro-6-(2-iminopyrrolidin-1-yl)methyl-2,4(1H,3H)-pyrimidinedione hydrochloride exhibiting characteristic peaks at angles of 11.6°, 17.2°, 17.8°, 23.3°, 27.1°, and 29.3° as a diffraction angle (2θ±0.1°) in powder X-ray diffraction.

9 Claims, 3 Drawing Sheets

STABLE CRYSTAL FORM OF TIPIRACIL HYDROCHLORIDE AND CRYSTALLIZATION METHOD FOR THE SAME

TECHNICAL FIELD

The present invention relates to a stable crystal form of tipiracil hydrochloride having excellent preservation stability and being useful as an active ingredient of medicaments, and a crystallization method for the same.

BACKGROUND ART

Generally, when a compound is used as an active ingredient for medicaments, the compound is required to have chemical and physical stability for preservation of stable quality and/or easy storage and management. For the reason, such a compound is preferably produced in a stable crystal form. Also, when a compound is used as an active pharmaceutical ingredient in a drug, the most stable crystal form of the compound is selected. Moreover, Guideline for Residual Solvents in ICH (International Conference on Harmonisation of Technical Requirements for Registration of Pharmaceuticals for Human Use) guidelines makes recommendations regarding which of various solvents should be avoided/limited/used and the acceptable amounts thereof. Some solvents used in producing medicaments are toxic, and therefore, in view of safety, the amount of such a solvent remaining after a production process is desirably as small as possible. Moreover, medicaments may become charged with static electricity in the production process. Charged medicaments can adhere to a production machine, a dividing and packing machine, and the like and problems of yield deterioration and unequal packing occur. To avoid such problems, medicaments having low chargeability are preferred.

Patent Literature 1 discloses that one of uracil derivatives, tipiracil hydrochloride (chemical name: 5-chloro-6-(2-iminopyrrolidin-1-yl)methyl-2,4(1H,3H)-pyrimidinedione hydrochloride, hereinafter sometimes referred to as "TPI" (5-chloro-6-(2-iminopyrrolidin-1-yl)methyl-2,4(1H,3H)-pyrimidinedione is sometimes referred to as "tipiracil")) represented by the following Formula (1)

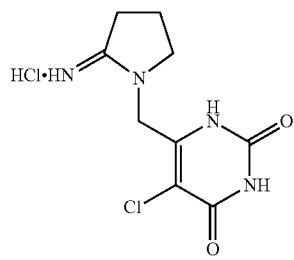

(1)

has an inhibitory action on human thymidine phosphorylase and an enhancing action on the antitumor effect of trifluridine (hereinafter sometimes referred to as "FTD"). An antitumor agent "TAS-102" composed of a mixture of FTD and TPI with a molar ratio of 1 to 0.5, which is currently still under development as an oral preparation, has already been approved, in Japan, as a therapeutic agent for advanced or recurrent colorectal cancer (Non-patent Literature 1 and 2). Examples of previously reported methods for producing tipiracil hydrochloride include a method in which tipiracil monohydrochloride 1/10 hydrate is obtained as follows: 5-chloro-6-chloromethyluracil, 2-iminopyrrolidine, and a solution of sodium ethoxide in N,N-dimethylformamide are stirred at room temperature for 14 hours; the crystallized material is separated by filtration and suspended in water; the suspension is neutralized with acetic acid; the insoluble matter is separated by filtration and dissolved in 1 N hydrochloric acid; activated carbon is added thereto; the mixture is filtered; the filtrate is concentrated under reduced pressure; and the residue is washed with ethanol and separated by filtration (Patent Literature 1). In another reported method, tipiracil hydrochloride is produced as follows: 2-iminopyrrolidine hydrochloride, 1,8-diazabicyclo[5.4.0]undec-7-ene (DBU), and 5-chloro-6-(chloromethyl)pyrimidine-2,4-(1H,3H)-dione are allowed to react in methanol; the resulting precipitate is dissolved in 2 N hydrochloric acid at a temperature of 90° C. with heating; ethanol is added to the reaction liquid; and the liquid is left to stand at room temperature to give white crystals (Non-patent Literature 3). However, it has turned out later that the white crystals obtained by these methods were mixed crystals containing Crystal III described below.

At present, there is no known method by which a stable crystal form of highly-pure anhydrous tipiracil hydrochloride can be obtained with a high reproducibility.

CITATION LIST

Patent Literature

PTL 1: WO 96/30346

Non-Patent Literature

NPL 1: International Journal of Oncology 25: 571-578, 2004
NPL 2: Invest New Drugs 26(5): 445-54, October 2008
NPL 3: Bioorganic & Medicinal Chemistry 12 (2004) 3443-3450

SUMMARY OF INVENTION

Technical Problem

An objective of the present invention is to provide a stable crystal form of tipiracil hydrochloride useful as an active ingredient of medicaments.

Solution to Problem

The present inventors have wholeheartedly carried out investigations, and found the following: tipiracil hydrochloride has three crystal forms (Crystal I, Crystal II, and Crystal III); Crystal I and Crystal III are superior to Crystal II in preservation stability; and Crystal I is, in comparison to Crystal III, safer as a medicament because of its smaller residual solvent content and easier to handle because of its smaller electric charge amount. Moreover, the present inventors performed experiments under an extremely large number of combinations of conditions such as the kind of solvent, temperature, concentration, resting and cooling time, stirring time, and stirring rate, and through trial and error, found a production method for advantageously obtaining a highly-pure Crystal I under specific conditions. As a result of further investigations, they completed the present invention.

That is, the present invention relates to the following (1) to (14).

(1) A crystal of 5-chloro-6-(2-iminopyrrolidin-1-yl)methyl-2,4(1H,3H)-pyrimidinedione hydrochloride exhibiting peaks at two or more angles selected from the group consisting of 11.6°, 17.2°, 17.8°, 23.3°, 27.1°, and 29.3° as a diffraction angle (2θ±0.1°) in powder X-ray diffraction.

(2) The crystal according to the above (1), exhibiting peaks at angles of 11.6°, 17.2°, 17.8°, 23.3°, 27.1°, and 29.3° as a diffraction angle (2θ±0.1°) in powder X-ray diffraction.

(3) The crystal according to the above (1) or (2), exhibiting an endothermic peak determined by thermogravimetry-differential thermal analysis at a temperature of around 262° C.

(4) The crystal according to any of the above (1) to (3), which shows, in single-crystal analysis, the following crystal data:
Crystal system: monoclinic system.
Space group: $P2_1/n$ (No. 14)
Lattice constant:
a=11.6006 (9) Å
b=10.3106 (11) Å
c=10.3036 (10) Å
α=90°
β=101.951 (7)°
γ=90°
Unit lattice volume: 1205.7 (2) Å$^3$.

(5) The crystal according to any of the above (1) to (4), in an anhydrous form.

(6) The crystal according to any of the above (1) to (5), having a purity of 90% by mass or more.

(7) The crystal according to any of the above (1) to (6), exhibiting peaks at two or more angles selected from the group consisting of 11.6°, 17.2°, 17.8°, 23.3°, 27.1°, and 29.3° as a diffraction angle (2θ±0.1°) in powder X-ray diffraction after a 6-month preservation at 40° C. in a stability test.

(8) A crystal of 5-chloro-6-(2-iminopyrrolidin-1-yl)methyl-2,4(1H, 3H)-pyrimidinedione hydrochloride exhibiting peaks at two or more angles selected from the group consisting of 10.5°, 19.6°, 23.7°, 26.2°, and 31.2° as a diffraction angle (2θ±0.1°) in powder X-ray diffraction.

(9) The crystal according to the above (8), exhibiting peaks at angles of 10.5°, 19.6°, 23.7°, 26.2°, and 31.2° as a diffraction angle (2θ±0.1°) in powder X-ray diffraction.

(10) The crystal according to the above (8) or (9), exhibiting an endothermic peak determined by thermogravimetry-differential thermal analysis at a temperature of around 245° C.

(11) The crystal according to any of the above (8) to (10), which shows, in single-crystal analysis, the following crystal data:
Crystal system: monoclinic system
Space group: $P2_1$
Lattice constant:
a=10.3221 (14) Å
b=9.8634 (13) Å
c=11.6643 (16) Å
α=90°
β=100.317°
γ=90°
Unit lattice volume: 1169.5 (3) Å$^3$.

(12) The crystal according to any of the above (8) to (11), in an anhydrous form.

(13) A production method of the crystal according to any of the above (1) to (7), comprising,
dissolving 5-chloro-6-(2-iminopyrrolidin-1-yl)methyl-2,4(1H,3H)-pyrimidinedione hydrochloride in a water-ethanol mixed solvent with heating, and
subjecting the solution to crystallization at a temperature of 40° C. or higher, followed by cooling.

(14) A pharmaceutical composition comprising the crystal according to any one of the above (1) to (12) and a pharmaceutically acceptable carrier.

Advantageous Effects of Invention

Crystal I and Crystal III as the tipiracil hydrochloride according to the present invention have excellent preservation stability. Therefore, these crystal forms are more excellent compared to other crystal forms in view of, for example, purity, handleability (lower hygroscopicity), fluidity, grindability, and/or quality control, and are useful as crystals appropriate for pharmaceutical formulation.

Crystal I and Crystal III of the present invention having the above-described remarkable preservation stability characteristic of the present invention retains the excellent stability even in contact with heat, light, oxygen, humidity, or other molecules (e.g. FTD). Furthermore, Crystal I and Crystal III of the present invention are excellent in filtration performance, drying characteristics, and fluidity, and can be produced in an industrially advantageous manner.

Moreover, Crystal I of the present invention, in which the amount of residual solvent is below the reference value described in the Guideline for Residual Solvents in ICH (International Conference on Harmonisation of Technical Requirements for Registration of Pharmaceuticals for Human Use) guidelines, is safe as a medicament. Furthermore, Crystal I, having a smaller electric charge amount, is easier to handle in the production and packing of medicaments, compared to Crystal III.

DESCRIPTION OF EMBODIMENTS

Figure 1:
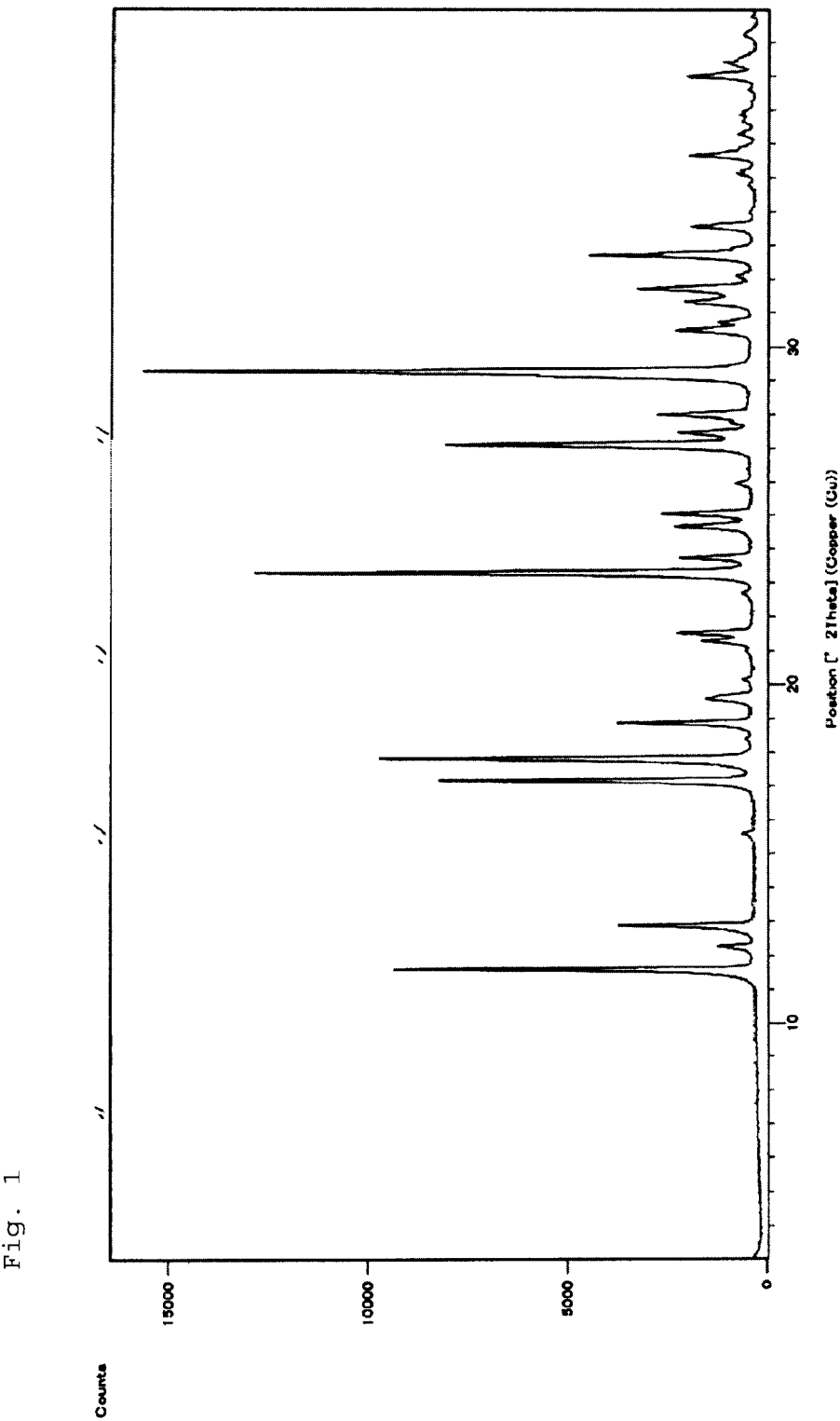
FIG. 1 shows a powder X-ray diffraction chart of Crystal I.

Crystal I of the present invention in anhydrous form can be produced with high purity by a method in which tipiracil hydrochloride (hereinafter sometimes referred to as "Compound (1)") is dissolved in a water-ethanol mixed solvent with heating, and the solution is subjected to crystallization at a temperature of 40° C. or higher and then is cooled.

The Compound (1) to be used in the crystallization method of the present invention may be, for example, one produced by adding hydrochloric acid to a free base of Compound (1) in accordance with the method described in WO 96/30346. The Compound (1) to be used may be in an uncrystallized state after the synthesis thereof or one once taken out as crystals (crude crystals). However, for a further increased crystal purity, Compound (1) once taken out as crystals is preferred. The crystals may be in any form of Crystal I, Crystal II, and Crystal III.

The mixing ratio of a water-ethanol mixed solvent can be selected as appropriate, and the ratio (v/v) of water and ethanol is preferably 1:1 to 1:10, more preferably 1:2 to 1:6, and particularly preferably 1:4. At the time of the use of the water-ethanol mixed solvent, preferably, a solution obtained by dissolving Compound (1) in water with heating is added to ethanol in an amount determined so that the above ratio is achieved. The concentration of the Compound (1) is not particularly limited, but is preferably 1 to 15% (w/v) in the solution of Compound (1) in water-ethanol.

To produce Crystal I of high purity, temperature control of the solution of Compound (1) in water-ethanol during the crystallization process is extremely important. The solution temperature for the crystallization is 40° C. and higher, and preferably 44 to 63° C. The duration of the crystallization can be set as appropriate. When the temperature is low, the time can be set long, and when the temperature is high, the time can be set short. For example, the time can be set to 1.5 hours or more when the temperature is in the range of 44 to 50° C., and it can be set to 0.5 hour or more when the temperature is in the range of 50 to 63° C. In view of production efficiency, the solution is preferably maintained at a temperature of 44 to 55° C. for 1.5 to 7 hours (more preferably for 1.5 to 3 hours), or at a temperature of 50 to 63° C. for 0.5 to 7 hours (more preferably for 0.5 to 3 hours). When the temperature is 40° C. or lower, Crystal II, which is poor in long-term storage stability, is precipitated. When the temperature is 63° C. or higher, the amount of decomposition products of Compound (1) is large, and accordingly, a temperature of lower than 63° C. is preferred for efficiently producing Crystal I containing less impurities.

An appropriate amount of Crystal I of Compound (1) or of mixed crystals containing Crystal I may be added as seed crystals for accelerating crystallization. The amount of the seed crystal to add is 0.01 to 5% (w/v) relative to the solvent amount, and preferably 0.03 to 1% (w/v). The mixed crystals containing Crystal I means a mixture containing 25% or more of Crystal I. Moreover, for a reduction in crystallization time and particle diameter control, the crystallization may be allowed to proceed with stirring.

The present inventors carried out investigations about combinations of a large number of factors, such as pH, concentration, temperature, and stirring time, which may affect the generation of Crystal I of Compound (1) in the production thereof. As a result of trial and error, the inventors found that the following method is particularly preferred from the industrial viewpoint, that is, from the viewpoints of process control, required time, crystal purity, reproducibility, etc. Use of a seed crystal is, of course, not indispensable. The preferred method for producing Crystal I is described in detail below. Crystal I can be produced by a method in which crystals of Compound (1) are dissolved in water with heating, the solution is added to ethanol so that the ratio (v/v) of water and ethanol is 1:1 to 1:10, and the mixture is stirred at a temperature of 44 to 63° C. and then is cooled. More preferably, Crystal I can be produced by a method in which crystals of Compound (1) are dissolved in water with heating, the solution is added to ethanol so that the ratio (v/v) of water and ethanol is 1:2 to 1:6, the mixture is stirred at a temperature of 44 to 50° C. for 1.5 to 7 hours or at a temperature of 50 to 63° C. for 0.5 to 7 hours and then is cooled for 0.5 hour or more, and resulting Crystal I is collected. This crystallization method can efficiently produce anhydrous Crystal I of Compound (1) of high purity without the influence of chance factors. Additionally, it is a common knowledge in the field of chemistry that, even with many efforts, obtaining a novel excellent crystal cannot be achieved without relying on chances.

Moreover, Crystal III of Compound (1) of high purity can be produced in accordance with Example 2. "High purity" used in the present invention means that at least 90% by mass, preferably 95% by mass, and more preferably 99% by mass of the crystals of Compound (1) are the crystals of the present invention.

"Cooling" used in the present invention means that the temperature of a solution is maintained at 40° C. or lower, and preferably at 15° C. or lower. The cooling time is preferably 0.5 hours or more, and more preferably 1 hour or more.

The precipitated crystals can be isolated and purified from the above-described solution, where the crystals are dissolved in a solvent or a mixed solvent, by a known method for isolation and purification, such as filtration, washing with an organic solvent, and drying under reduced pressure. Examples of the organic solvent used for the washing include lower alcohols, acetone, and acetonitrile.

As shown in FIG. 1, the powder X-ray diffraction pattern of the thus obtained crystal of the present invention (Crystal I) shows characteristic peaks at angles of 11.6°, 17.2°, 17.8°, 23.3°, 27.1°, and 29.3° as a diffraction angle (2θ±0.1°). Therefore, the crystal of the present invention (Crystal I) is a crystal of tipiracil hydrochloride exhibiting peaks at two or more angles selected from the group consisting of 11.6°, 17.2°, 17.8°, 23.3°, 27.1°, and 29.3° as a diffraction angle (2θ±0.1°) in powder X-ray diffraction. The crystal is preferably a crystal of tipiracil hydrochloride exhibiting peaks at three or more angles selected from the group consisting of 11.6°, 17.2°, 17.8°, 23.3°, 27.1°, and 29.3° as a diffraction angle (2θ±0.1°), and particularly preferably a crystal of tipiracil hydrochloride exhibiting peaks at angles of 11.6°, 17.2°, 17.8°, 23.3°, 27.1°, and 29.3° as a diffraction angle (2θ±0.1°) in powder X-ray diffraction. Moreover, the results of thermogravimetry-differential thermal analysis (TG/DTA) show an endothermic peak at a temperature of around 262° C.

Figure 2:
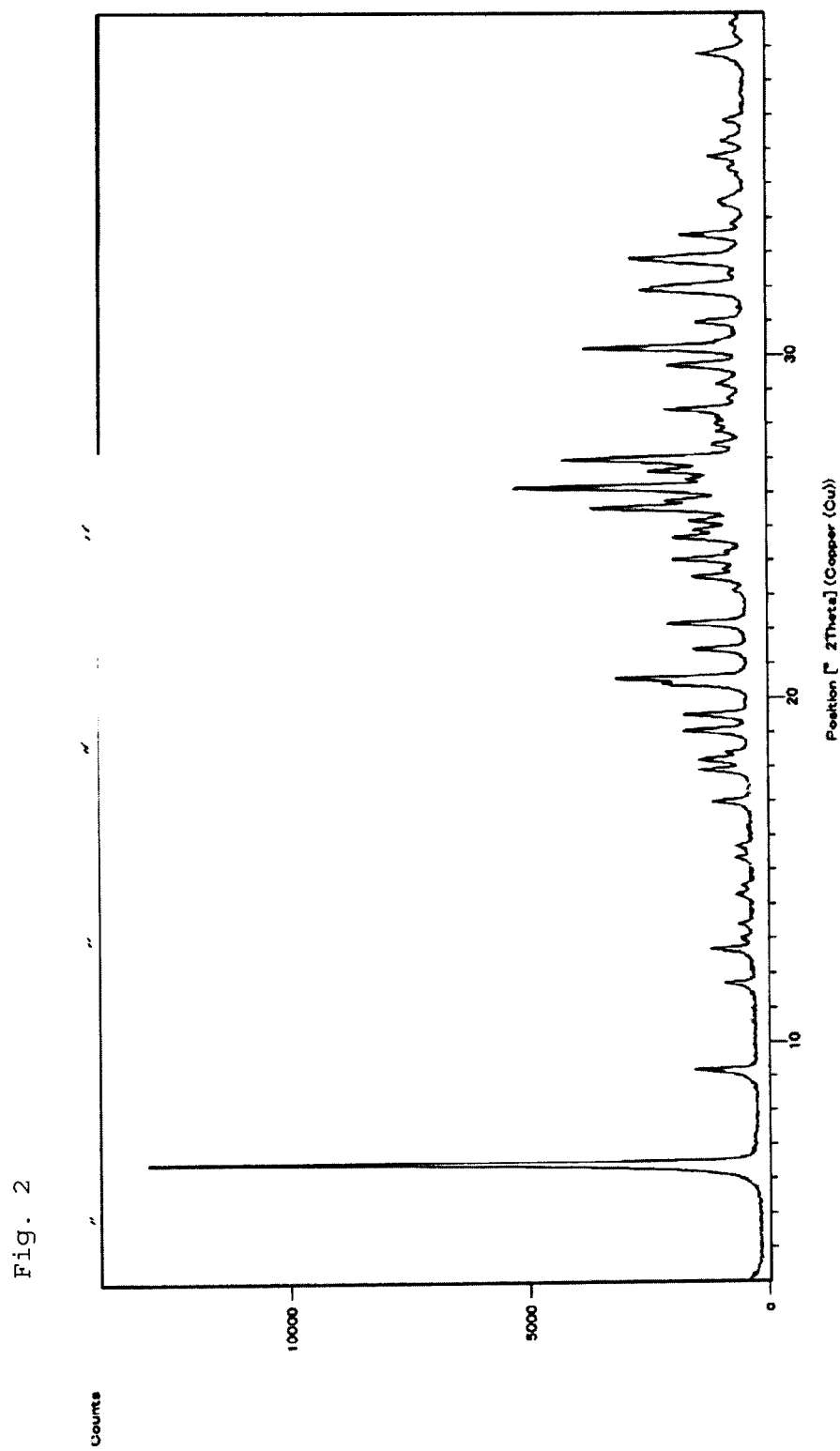
FIG. 2 shows a powder X-ray diffraction chart of Crystal II.

In contrast, as shown in FIG. 2, the powder X-ray diffraction pattern of Crystal II shows characteristic peaks at angles of 6.5°, 20.6°, 25.5°, 26.1°, 27.0°, and 30.2° as a diffraction angle (2θ±0.1°). Moreover, the results of TG/DTA show no definite endothermic peak.

Figure 3:
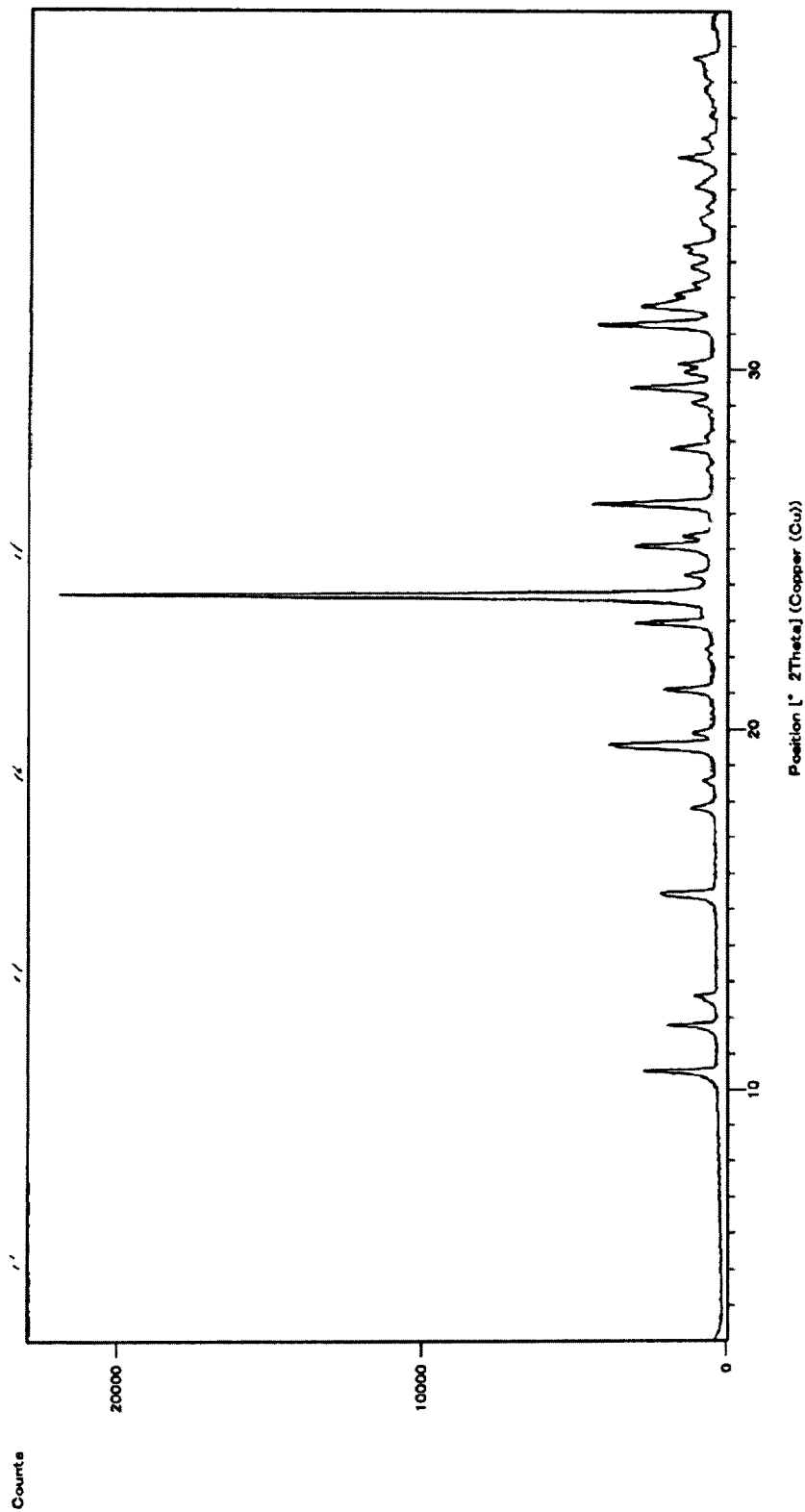
FIG. 3 shows a powder X-ray diffraction chart of Crystal III.

As shown in FIG. 3, the powder X-ray diffraction pattern of Crystal III shows characteristic peaks at angles of 10.5°, 19.6°, 23.7°, 26.2°, and 31.2° as a diffraction angle (2θ±0.1°) in powder X-ray diffraction. Therefore, the crystal of the present invention (Crystal III) is a crystal of tipiracil hydrochloride exhibiting peaks at two or more angles selected from the group consisting of 10.5°, 19.6°, 23.7°, 26.2°, and 31.2° as a diffraction angle (2θ±0.1°) in powder X-ray diffraction. The crystal is preferably a crystal of tipiracil hydrochloride exhibiting peaks at three or more angles selected from the group consisting of 10.5°, 19.6°, 23.7°, 26.2°, and 31.2° as a diffraction angle (2θ±0.1°) and particularly preferably a crystal of tipiracil hydrochloride exhibiting peaks at angles of 10.5°, 19.6°, 23.7°, 26.2°, and 31.2° as a diffraction angle (2θ±0.1°) in powder X-ray diffraction. Moreover, the results of TG/DTA show an endothermic peak at a temperature of around 245° C.

Each peak value in a powder X-ray diffraction spectrum may have a margin of error attributable to measuring equipment or measurement conditions such as peak reading conditions. Herein, each peak value may have a measurement error within the range of about ±0.2°.

The temperature of the endothermic peak (peak top value) measured in TG/DTA may vary with the temperature increase per minute, the purity of the sample, or the like. The term "around" used herein means ±5.0° C.

The crystal of the present invention has extremely high storage stability, an advantage in quality control, and also excellent handleability. In particular, as shown in examples described below, even after long-term storage under high-temperature and high-humidity conditions, Crystal I and Crystal III hardly contain analogous substances and show no change in their crystal forms. In contrast, Crystal II has a poor long-term storage stability, which becomes a problem in its use as a medicaments, and therefore is undesirable. Crystal I of the present invention is superior to Crystal III because of its smaller residual solvent content and smaller electric charge amount. As shown in examples described below, Crystal III contains the solvent used for the production in an amount above the reference value described in the Guideline for Residual Solvents in ICH guidelines, and therefore is undesirable as a medicament. In contrast, Crystal I contains residual solvent in an amount below the reference value and has high safety, and therefore is preferred as a medicament. Moreover, as shown in examples described below, Crystal I, which has a smaller electric charge amount compared to Crystal III, hardly adheres to production machines or packages in the production, the packing, and the use of medicaments, leading to easy production and handling.

The crystal of the present invention can be processed, directly or after grinding, into pharmaceutical compositions in various forms such as oral preparations including a tablet, a capsule, a granule, a subtle granule, a powder, and a dry syrup, external preparations including a suppository, an inhalant, a nasal drop, an ointment, a plaster, and an aerosol agent, and an injection. The crystal is preferably used for oral preparations. These pharmaceutical compositions can be produced using a pharmaceutically acceptable carrier by a preparation method known to those skilled in the art. When an oral solid preparation is prepared, an excipient and, as necessary, a binder, a disintegrant, a lubricant, a colorant, a flavoring agent, an odor masking agent, and the like are added to the active ingredient and then a tablet, a coated tablet, a granule, a powder, a dry syrup, a capsule, and the like can be produced by a conventional method. When an oral liquid preparation is prepared, a flavoring agent, a buffer, a stabilizer, an odor masking agent, and the like are added to an active ingredient and then an oral liquid medicine, a syrup, and the like can be produced by a conventional method. When an injection is prepared, a pH adjuster, a buffer, a stabilizer, a tonicity agent, a local anesthetic, and the like are added to an active ingredient and then a hypodermic injection, an intramuscular injection, and an intravenous injection can be produced by a conventional method. When a rectal suppository is prepared, an excipient and, as necessary, a surfactant and the like are added to an active ingredient and then a suppository can be produced by a conventional method. When an ointment or a preparation in the form of, for example, paste, cream, or gel is prepared, a base, a stabilizer, a moistening agent, a preservative, and the like which are generally used are added as necessary, and are, by a conventional method, mixed and prepared. As the base, for example, a white petrolatum, paraffin, glycerin, cellulose derivatives, polyethylene glycol, silicones, bentonite, and the like can be used. As the preservative, methyl parahydroxybenzoate, ethyl parahydroxybenzoate, propyl parahydroxybenzoate, and the like can be used. When an adhesive skin patch is produced, the above ointment, cream, gel, paste, or the like is applied onto a normal support medium by a conventional method. As the support medium, woven fabrics and nonwoven fabrics comprising cotton, a staple fiber, and a chemical fiber, and films and foam sheets comprising flexible polyvinyl chloride, polyethylene, and polyurethane are suitable.

These pharmaceutical compositions are useful as an agent for enhancing the antitumor effects of trifluorothymidine (FTD), an agent for reducing the side-effects caused of chemotherapy, an anti-HIV agent, an agent for treatment of inflammatory bowel disease, and an agent for enhancing the effects of radiation therapy (WO 96/30346, WO 00/56337, WO 01/34162, WO 07/122812, and WO 2008/001502).

The amount of Crystal I to be compounded in the above pharmaceutical composition varies according to the symptoms of the patient to be administered, the preparation form, or the like. For the reason, the amount of Crystal I to be compounded is not fixed, but generally, about 5 to 1000 mg of Crystal I is desirably contained in an oral preparation, about 0.1 to 500 mg is desirably contained in an injection, and about 5 to 1000 mg is desirably contained in a suppository or an external preparation, per dosage unit. Similarly, the daily dose of Crystal I in the pharmaceutical composition also varies according to the symptoms, the administration route, the age of the patient, and the like. Therefore, the dose cannot be determined in a fixed manner and is determined according to a prescription by a doctor. Generally preferred dose is about 0.1 to 5000 mg.

EXAMPLES

The production method of the present invention is specifically described with reference to Examples, Reference Examples, and Test Examples hereinbelow, but the present invention is not limited thereto.

Powder X-ray diffraction data were measured in accordance with the following test conditions after a suitable amount of a test substance was slightly crushed in an agate mortar, as necessary.

Target: Cu
X-ray tube current: 40 mA
X-ray tube voltage: 45 kV
Scanning range: 2θ=3.0 to 40.0°
Step: 2θ=0.01671
Average time/step: 10.160 s
Variable divergence slit: radiation length=15 mm A thermogravimetry-differential thermal analysis (TG/DTA) study was conducted on about 10 mg of the test substance in accordance with the following test conditions.

Sample container: aluminum container
Temperature rising rate: After 5 min at 25° C., 10° C./min from 25 to 300° C.
Atmosphere gas: nitrogen (100 mL/min)
Control substance: α-alumina Moreover, the infrared absorption spectrum (IR) was measured in accordance with the following test conditions.

Number of integration steps: 20 steps
Resolution: 2 $cm^{-1}$
Transparency range: 0 to 100%
Measurement method: KBr pellet method Example 1

Production of Crystal I of Tipiracil Hydrochloride (1) First, 100 mL of 6 N hydrochloric acid and 220 mL of water were mixed, and 95.1 g of tipiracil obtained in accordance with the method described in WO 96/30346 was dissolved therein with heating. The solution was hot filtered at a temperature of around 60° C. and then 1280 mL of ethanol was added thereto. The mixture was maintained at a temperature of around 60° C. for 2 hours by heating and was cooled with ice. The resulting crystals were separated by filtration, and thus 89.3 g of anhydrous Crystal I of tipiracil hydrochloride was obtained (recovery rate: 82%). The powder X-ray diffraction pattern of the obtained crystal showed characteristic peaks at angles of 11.6°, 17.2°, 17.8°, 23.3°, 27.1°, and 29.3° as a diffraction angle (2θ±0.1°), as is the case with the pattern in FIG. 1. Moreover, the $^1$H-NMR spectrum (DMSO-d6, tetramethylsilane (TMS)) of the obtained crystal showed that the amount of residual ethanol contained in the crystals was below the reference value (5000 ppm) described in the Guideline for Residual Solvents in ICH guidelines.

(2) Tipiracil hydrochloride obtained in accordance with the method described in WO 96/30346 was dissolved in water with heating. The solution was hot filtered at a temperature of around 60° C. and then ethanol and the seed crystal (Crystal I) obtained in the above (1) were added thereto. The mixture was maintained at a temperature of around 60° C. for 2 hours by heating. The resulting crystals were separated by filtration, and thus anhydrous Crystal I of tipiracil hydrochloride was obtained. The powder X-ray diffraction pattern of the obtained crystal showed characteristic peaks at angles of 11.6°, 17.2°, 17.8°, 23.3°, 27.1°, and 29.3° as a diffraction angle (2θ±0.1°), as shown in FIG. 1. Moreover, the results of TG/DTA show an endothermic peak at a temperature of 262.2° C.

Example 2

Production of Crystal III of Tipiracil Hydrochloride (1) In 20 mL of 6 N hydrochloric acid and 230 mL of water, 22.0 g of tipiracil obtained in accordance with the method described in WO 96/30346 was dissolved. The solution was filtered and then concentrated, and 100 mL of ethanol was added thereto at room temperature. The resulting crystals were separated by filtration, and thus 19.7 g of Crystal III of tipiracil hydrochloride was obtained (recovery rate: 78%). The powder X-ray diffraction pattern of the obtained crystal showed characteristic peaks at angles of 10.5°, 19.6°, 23.7°, 26.2°, and 31.2° as a diffraction angle (2θ±0.1°, as is the case with the pattern in FIG. 3. Moreover, the $^1$H-NMR spectrum (DMSO-d6, TMS) of the obtained crystal showed that the amount of ethanol contained in the crystals was 16000 ppm. This value exceeds the reference value (5000 ppm) for ethanol described in the Guideline for Residual Solvents in ICH guidelines.

(2) Tipiracil obtained in accordance with the method described in WO 96/30346 was dissolved in ethanol and concentrated hydrochloric acid was added thereto. The mixture was stirred at a temperature of 64° C. for 1 hour and was cooled to a temperature of 30° C. The resulting crystals were separated by filtration and washed with methanol, and thus Crystal III of tipiracil hydrochloride was obtained. The powder X-ray diffraction pattern of the obtained crystal showed characteristic peaks at angles of 10.5°, 19.6°, 23.7°, 26.3°, and 31.3° as a diffraction angle (2θ±0.1°), as shown in FIG. 3. Moreover, the results of TG/DTA show an endothermic peak at a temperature of 245.1° C. Furthermore, the results of gas chromatography (a headspace method) analysis of the obtained crystal show that the amount of methanol contained in the crystals was 49862 ppm. This value exceeds the concentration limit value (3000 ppm) for ethanol described in the Guideline for Residual Solvents in ICH guidelines.

Reference Example 1

Production of Crystal II of Tipiracil Hydrochloride (1) First, 50 mL of 6 N hydrochloric acid and 500 mL of water were mixed, and 61.5 g of tipiracil obtained in accordance with the method described in WO 96/30346 was dissolved therein. The solution was treated with activated carbon, filtered, and then concentrated, and 200 mL of ethanol was added thereto at room temperature. The resulting crystals were separated by filtration, and thus 57.9 g of hydrous Crystal II of tipiracil hydrochloride was obtained (recovery rate: 77%). The powder X-ray diffraction pattern of the obtained crystal showed characteristic peaks at angles of 6.5°, 20.6°, 25.5°, 26.1°, 27.0°, and 30.2° as a diffraction angle (2θ±0.1°), as is the case with the pattern in FIG. 2. Moreover, the $^1$H-NMR spectrum (DMSO-d6, TMS) of the obtained crystal showed that the amount of residual ethanol contained in the crystals was below the reference value (5000 ppm) described in the Guideline for Residual Solvents in ICH guidelines.

(2) Tipiracil hydrochloride obtained in accordance with the method described in WO 96/30346 was added to water and was dissolved at a temperature of 60° C. The solution was filtered and then added to ethanol being cooled with ice. The resulting crystals were separated by filtration, and thus Crystal II of tipiracil hydrochloride was obtained. The powder X-ray diffraction pattern of the obtained crystal showed characteristic peaks at angles of 6.5°, 20.6°, 25.7°, 26.2°, 27.0°, and 30.2° as a diffraction angle (2θ±0.1°), as shown in FIG. 2. Moreover, the results of TG/DTA show no definite endothermic peak.

Example 3

Stability Test

Crystal I, Crystal III, and Crystal II of tipiracil hydrochloride obtained in accordance with Example 1, Example 2, and Reference Example 1 respectively were tested for storage stability after preservation at a temperature of 40° C. for six months.

The results revealed that Crystal I and Crystal III are extremely stable because no change was found in the powder X-ray diffraction patterns of the crystals. Moreover, the amounts of analogous substances in Crystal I and Crystal III were small and not increased even after the elapse of 6 months.

In contrast, the powder X-ray diffraction pattern of Crystal II was not the same, revealing that Crystal II is unstable.

Example 4

Examination of Crystallization Conditions

The influences of the crystallization temperature and crystallization time on the crystal form of tipiracil hydrochloride in a crystal purification step was examined. In 240 mL of water, 60 g of the crystals of tipiracil hydrochloride obtained in accordance with Example 1, Example 2, or Reference Example 1 were dissolved with heating. The solution was divided into three parts and 320 mL of ethanol was added thereto. The prepared samples were subjected to crystallization under various conditions of temperature (32 to 63° C.) and time (0.5 to 3 hours). The crystal forms of the obtained crystals were determined by IR spectroscopy and DSC (differential scanning calorimetry). The results are shown in Table 1.

The results show that Crystal II, which is poor in storage stability, was obtained when the crystallization temperature was below 35° C. When the crystallization temperature was maintained at 44° C. or higher, Crystal I, which has high storage stability, was efficiently obtained with high purity.

TABLE 1

|  |  | Crystallization time | | |
|---|---|---|---|---|
|  |  | 0.5 h | 1.5 h | 3 h |
| Crystallization temperature | 60 to 63° C. | Crystal I | Crystal I | Crystal I |
|  | 44 to 50° C. | Crystal II | Crystal I | Crystal I |
|  | 32 to 35° C. | Crystal II | Crystal II | Crystal II |

Example 5

Single Crystal Analysis of Crystal I

To tipiracil hydrochloride, 1 mL of distilled water was added to dissolve the tipiracil hydrochloride. Ethanol was slowly mixed therein by vapor diffusion at room temperature. Two weeks later, precipitation of Crystal I was confirmed.

Crystal size: 0.10×0.20×0.25 mm
Crystal color: colorless
Crystal form: plate-like Measurements were performed under the following measurement conditions and the data were processed using teXsan (Ver.2.0), a structure analysis software manufactured by Rigaku Corporation.

X-ray source: CuK α radiation
With use of crystal monochromator (graphite)
Output 50 kV, 150 mA
Collimator diameter: 0.5 mm
Detector: scintillation counter
Attenuator: Ni foil (factor=9.15)
Light-receiving slit: horizontal slit
Scanning method: ω-2θ scan
Scanning speed: 16.0°/min (in omega)
Maximum number of repeated scanning steps: 3 times ($I<15.0\sigma$ (I))
Scanning width: $(1.58+0.30 \tan \theta)°$
2θ max: 149.9°
Number of measured reflections: 4697
Number of unique reflections: 2474 (Rint=0.020)
Data correction: Lorentz factor, polarization factor
Absorption correction: correction with ψscan (correction coefficient: 0.64 to 1.00)
Measurement temperature: 18 to 19° C.
Measurement frequency of standard reflection: every 150 reflections The crystal data are shown below.
Crystal system: monoclinic system
Space group: $P2_1/n$ (No. 14)
Lattice constant:
a=11.6006 (9) Å
b=10.3106 (11) Å
c=10.3036 (10) Å
α=90°
β=101.951 (7)°
γ=90°
Unit lattice volume: 1205.7 (2) Å³

Example 6

Single Crystal Analysis of Crystal III

In an aluminum-block precision thermostatic bath (CHILL HEAT CHT-100 manufactured by IWAKI) set at a temperature of 70° C., 300 μL of methanol aqueous solution (MeOH/H$_2$O=1/1 (v/v)) was added to 19.6 μg of tipiracil hydrochloride to dissolve the tipiracil hydrochloride. The solution was slowly cooled to room temperature and was allowed to stand at a temperature of 20° C. in a program low constant temperature incubator (Program Incubator IN61 manufactured by Yamato). Eight days later, a rhombic plate crystal was obtained.

Crystal size: 0.45×0.4×0.15 mm
Crystal form: rhombic plate-like

The obtained single crystal was fixed to a mounting pin and the X-ray diffraction intensity was measured. Measurements for crystal structure analysis were performed using a two-dimensional X-ray diffractometer manufactured by Bruker, SMART1000 (MoK α, 50 kV; 40 mA) and a 0.5 mm collimator, at room temperature, with omega scan, with a scanning width of 0.3°, and with an exposure time of 10 seconds. The crystal structure was determined by a direct method using a program SHELXL-97 and the structure was refined by full-matrix least squares method using the program SHELXL-97.

The crystal data are shown below.
Crystal system: monoclinic system
Space group: $P2_1$
Lattice constant:
a=10.3221 (14) Å
b=9.8634 (13) Å
c=11.6643 (16) Å
α=90°
β=100.317°
γ=90°
Unit lattice volume: 1169.5 (3) Å³

Example 7

Test for Measurement of Electric Charge Amount

Electric charge amounts of Crystal I and Crystal III obtained in accordance with Example 1 and Example 2 respectively were measured by air transfer. Crystal I or Crystal III was put in a powder supply part of an electrifying tube (made of SUS, 24.6×500 mm), and was left for 10 minutes. The sample was transferred by air at a flow rate of 130 L/min and the electric charge amount was calculated from the current value at that time obtained from the electrifying tube.

$$Q=-\int_0^t I dt$$

Q: Amount of electric charge [C]
I: Current generated during measurement [A]
t: Measuring time [t]

The measurement was performed 5 times, of which 3 times that gave stable results were adopted. The average of the values of the 3 times was regarded as the measured value. The results are shown below.

TABLE 2

(Crystal I)

| No. | Sample amount (g) | Amount of electric charge (C) | Amount of electric charge per unit mass (C/g) |
|---|---|---|---|
| 1 | 0.4963 | $5.3 \times 10^{-8}$ | $1.1 \times 10^{-7}$ |
| 2 | 0.5133 | $5.0 \times 10^{-8}$ | $9.7 \times 10^{-8}$ |
| 3 | 0.5217 | $5.1 \times 10^{-8}$ | $9.8 \times 10^{-8}$ |
| Average value | — | — | $1.0 \times 10^{-7}$ (positively-charged relative to SUS membrane) |

TABLE 3

(Crystal III)

| No. | Sample amount (g) | Amount of electric charge (C) | Amount of electric charge per unit mass (C/g) |
|---|---|---|---|
| 1 | 0.6244 | $2.0 \times 10^{-7}$ | $3.2 \times 10^{-7}$ |
| 2 | 0.4975 | $2.1 \times 10^{-7}$ | $4.2 \times 10^{-7}$ |
| 3 | 0.5650 | $1.8 \times 10^{-7}$ | $3.2 \times 10^{-7}$ |
| Average value | — | — | $3.5 \times 10^{-7}$ (positively-charged relative to SUS membrane) |

As shown in Table 2 and Table 3, Crystal III had three times as much charge as Crystal I had, revealing that Crystal III is likely to be charged.

The invention claimed is:

1. A crystal of 5-chloro-6-(2-iminopyrrolidin-1-yl)methyl-2,4(1H,3H)-pyrimidinedione hydrochloride, which is crystal Form I, exhibiting peaks at two or more angles selected from the group consisting of 11.6°, 17.2°, 17.8°, 23.3°, 27.1°, and 29.3° as a diffraction angle (2θ±0.1°) in powder X-ray diffraction.

2. The crystal according to claim 1, exhibiting peaks at angles of 11.6°, 17.2°, 17.8°, 23.3°, 27.1°, and 29.3° as a diffraction angle (2θ±0.1°) in powder X-ray diffraction.

3. The crystal according to claim 1, exhibiting an endothermic peak determined by thermogravimetry-differential thermal analysis at a temperature of around 262° C.

4. The crystal according to claim 1, which shows, in single-crystal analysis, the following crystal data:
    Crystal system: monoclinic system
    Space group: P2$_1$/n (No. 14)
    Lattice constant:
        a=11.6006 (9) Å
        b=10.3106 (11) Å
        c=10.3036 (10) Å
        α=90°
        β=101.951 (7)°
        γ=90°
Unit lattice volume: 1205.7 (2) Å$^3$.

5. The crystal according to claim 1, in an anhydrous form.

6. The crystal according to claim 1, having a purity of 90% by mass or more.

7. The crystal according to claim 1, exhibiting peaks at two or more angles selected from the group consisting of 11.6°, 17.2°, 17.8°, 23.3°, 27.1°, and 29.3° as a diffraction angle (2θ±0.1°) in powder X-ray diffraction after a 6-month preservation at 40° C. in a stability test.

8. A pharmaceutical composition comprising the crystal according to claim 1 and a pharmaceutically acceptable carrier.

9. A production method of the crystal according to claim 1, comprising,
    dissolving 5-chloro-6-(2-iminopyrrolidin-1-yl)methyl-2,4(1H,3H)-pyrimidinedione hydrochloride in a water-ethanol mixed solvent with heating, and
    subjecting the solution to crystallization at a temperature of 40° C. or higher, followed by cooling.

* * * * *

(12) EX PARTE REEXAMINATION CERTIFICATE (161st)
Ex Parte Reexamination Ordered under 35 U.S.C. 257

United States Patent
Kazuno et al.

(10) Number: US 9,527,833 C1
(45) Certificate Issued: *Sep. 16, 2019

(54) STABLE CRYSTAL FORM OF TIPIRACIL HYDROCHLORIDE AND CRYSTALLIZATION METHOD FOR THE SAME

(71) Applicant: TAIHO PHARMACEUTICAL CO., LTD., Tokyo (JP)

(72) Inventors: Hideki Kazuno, Ibaraki (JP); Tomonobu Mutsumi, Saitama (JP)

(73) Assignee: TAIHO PHARMACEUTICAL CO., LTD., Chiyoda-Ku, Tokyo (JP)

Supplemental Examination Request:
No. 96/000,268, Aug. 2, 2018

Reexamination Certificate for:
Patent No.: 9,527,833
Issued: Dec. 27, 2016
Appl. No.: 14/896,748
PCT Filed: Jun. 17, 2014
PCT No.: PCT/JP2014/065985
§ 371 (c)(1),
(2) Date: Dec. 8, 2015
PCT Pub. No.: WO2014/203877
PCT Pub. Date: Dec. 24, 2014

(*) Notice: This patent is subject to a terminal disclaimer.

(30) Foreign Application Priority Data

Jun. 17, 2013 (JP) .................. 2013-126567

(51) Int. Cl.
*C07D 403/06* (2006.01)

(52) U.S. Cl.
CPC ........ *C07D 403/06* (2013.01); *C07B 2200/13* (2013.01)

(58) Field of Classification Search
None
See application file for complete search history.

(56) References Cited

To view the complete listing of prior art documents cited during the supplemental examination proceeding and the resulting reexamination proceeding for Control Number 96/000,268, please refer to the USPTO's public Patent Application Information Retrieval (PAIR) system under the Display References tab.

*Primary Examiner* — Jerry D Johnson

(57) ABSTRACT

An objective of the present invention is to obtain a stable crystal form of 5-chloro-6-(2-iminopyrrolidin-1-yl)methyl-2,4(1H,3H)-pyrimidinedione hydrochloride. The present invention provides a crystal of 5-chloro-6-(2-iminopyrrolidin-1-yl)methyl-2,4(1H,3H)-pyrimidinedione hydrochloride exhibiting characteristic peaks at angles of 11.6°, 17.2°, 17.8°, 23.3°, 27.1°, and 29.3° as a diffraction angle (2θ±0.1°) in powder X-ray diffraction.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2 and 4 are cancelled.

Claims 1, 3, 6 and 7 are determined to be patentable as amended.

Claims 5, 8 and 9, dependent on an amended claim, are determined to be patentable.

New claims 10 and 11 are added and determined to be patentable.

1. A crystal of 5-chloro-6-(2-iminopyrrolidin-1-yl) methyl-2,4(1H,3H)-pyrimidinedione hydrochloride, which is crystal Form I, exhibiting peaks at two or more angles selected from the group consisting of 11.6°, 17.2°, 17.8°, 23.3°, 27.1°, and 29.3° as a diffraction angle (2θ±0.1°) in powder X-ray diffraction *and has crystal Form I purity of at least 90% by mass*.

3. [The crystal according to claim 1,] *A crystal of 5-chloro-6-(2-iminopyrrolidin-1-yl) methyl-2,4(1H,3H)-pyrimidinedione hydrochloride,* which is crystal Form I, *having a crystal Form I purity of at least 90% by mass,* exhibiting peaks at two or more angles selected from the group consisting of 11.6°, 17.2°, 17.8°, 23.3°, 27.1°, and 29.3° as a diffraction angle (2θ±0.1°) in powder X-ray diffraction, and exhibiting an endothermic peak determined by thermogravimetry-differential thermal analysis at a temperature of around 262° C.

6. The crystal according to claim 1, [having a] *wherein the* crystal form I purity [of 90%] *is 95%* by mass or more.

7. [The crystal according to claim 1,] *A Form I crystal of 5-chloro-6-(2-iminopyrrolidin-1-yl) methyl-2,4(1H,3H)-pyrimidinedione hydrochloride, having a crystal Form I purity of at least 90% by mass and* exhibiting peaks at two or more angles selected from the group consisting of 11.6°, 17.2°, 17.8°, 23.3°, 27.1°, and 29.3° as a diffraction angle (2θ±0.1°) in powder X-ray diffraction and after a 6-month preservation at 40° C. in a stability test.

*10. A Form I crystal of 5-chloro-6-(2-iminopyrrolidin-1-yl) methyl-2,4(1H,3H)-pyrimidinedione hydrochloride exhibiting peaks at two or more angles selected from the group consisting of 11.6°, 17.2°, 17.8°, 23.3°, 27.1°, and 29.3° which does not exhibit peaks at 6.5° and 10.5° as a diffraction angle (2θ±0.1°) in powder X-ray diffraction and has a crystal Form 1 purity of at least 90% by mass.*

*11. The crystal of claim 1, wherein the crystal form I purity is 99% by mass or more.*

\* \* \* \* \*